United States Patent
Hughes

(10) Patent No.: US 10,103,463 B1
(45) Date of Patent: Oct. 16, 2018

(54) IN-PLACE CLAMPING OF PIN-GRID ARRAY

(71) Applicant: ColdQuanta, Inc., Boulder, CO (US)

(72) Inventor: Steven Michael Hughes, Louisville, CO (US)

(73) Assignee: ColdQuanta, Inc., Boulder, CO (US)

( * ) Notice: Subject to any disclaimer, the term of this patent is extended or adjusted under 35 U.S.C. 154(b) by 0 days.

(21) Appl. No.: 15/825,600

(22) Filed: Nov. 29, 2017

Related U.S. Application Data

(60) Provisional application No. 62/564,475, filed on Sep. 28, 2017.

(51) Int. Cl.
| | |
|---|---|
| H01R 12/70 | (2011.01) |
| H01R 13/52 | (2006.01) |
| H01R 12/91 | (2011.01) |
| H01R 13/04 | (2006.01) |
| H01R 12/71 | (2011.01) |

(52) U.S. Cl.
CPC ..... *H01R 12/7076* (2013.01); *H01R 12/7011* (2013.01); *H01R 12/716* (2013.01); *H01R 12/91* (2013.01); *H01R 13/04* (2013.01); *H01R 13/5219* (2013.01)

(58) Field of Classification Search
CPC ............ H01R 12/7076; H01R 12/7011; H01R 12/717; H01R 23/7073; H01R 23/7084; H01R 12/88; H01R 12/91; H01R 23/6893; H01R 13/04
USPC ....................................... 439/278, 71, 83, 67
See application file for complete search history.

(56) References Cited

U.S. PATENT DOCUMENTS

| | | | |
|---|---|---|---|
| 4,688,152 A | 8/1987 | Chia | |
| 4,895,189 A | 1/1990 | Alemanni | |
| 4,916,523 A | 4/1990 | Sokolovsky | |
| 4,934,967 A | 6/1990 | Marks | |
| 5,006,922 A | 4/1991 | Mcshane | |
| 5,022,976 A | 6/1991 | Roll | |
| 5,103,292 A | 4/1992 | Mahulikar | |
| 5,144,412 A | 9/1992 | Chang | |
| 5,281,160 A | 1/1994 | Walkup et al. | |
| 5,290,193 A * | 3/1994 | Goff .................... | G01R 1/0483 439/331 |
| 5,304,735 A | 4/1994 | Earl | |
| 5,342,992 A | 8/1994 | Noto | |
| 5,380,212 A * | 1/1995 | Smeenge, Jr. ..... | H01R 13/2414 439/86 |
| 5,396,402 A | 3/1995 | Perugini | |
| 5,419,710 A * | 5/1995 | Pfaff .................... | G01R 1/0483 439/266 |
| 5,454,727 A | 10/1995 | Hsu | |

(Continued)

*Primary Examiner* — Harshad C Patel
(74) *Attorney, Agent, or Firm* — Clifton Leon Anderson

(57) ABSTRACT

An atomtronic (e.g., ultra-cold-matter physics or ion-trap) system includes a vacuum-cell structure, an integrated-circuit package with a pin-grid array, and a socket for interfacing the integrated-circuit package with external control and monitoring systems. After pins of the pin-grid array are inserted into holes of plates in the socket, the plates are moved in opposite directions so that contacts within the holes clamp in place the pins, providing electrical connections. The in-place clamping avoids stress at the seal between the integrated circuit package and the vacuum cell structure; thus, stress that could otherwise compromise the vacuum seal is avoided so as to yield a more reliable vacuum.

10 Claims, 9 Drawing Sheets

(56) References Cited

U.S. PATENT DOCUMENTS

| | | | |
|---|---|---|---|
| 5,516,416 A | 5/1996 | Canaperi | |
| 5,683,600 A * | 11/1997 | Kelley | B23K 26/06 |
| | | | 219/121.71 |
| 5,713,744 A * | 2/1998 | Laub | H05K 7/1061 |
| | | | 439/71 |
| 5,777,852 A | 7/1998 | Bell | |
| 5,850,691 A | 12/1998 | Bell | |
| 5,869,139 A | 2/1999 | Biggs | |
| 5,950,072 A | 9/1999 | Queyssac | |
| 6,099,321 A | 8/2000 | McHugh | |
| 6,181,149 B1 | 1/2001 | Godfrey | |
| 6,347,946 B1 | 2/2002 | Trobough | |
| 6,507,187 B1 | 1/2003 | Olivas | |
| 6,509,619 B1 | 1/2003 | Kendall | |
| 6,537,095 B1 | 3/2003 | Azuma | |
| 6,624,647 B2 * | 9/2003 | Adams | G01R 1/0483 |
| | | | 324/755.05 |
| 6,669,498 B2 | 12/2003 | Okita et al. | |
| 6,853,075 B2 | 2/2005 | Auner | |
| 7,118,385 B1 * | 10/2006 | Bodenweber | H05K 7/1061 |
| | | | 439/71 |
| 7,126,112 B2 | 10/2006 | Anderson et al. | |
| 7,344,383 B1 | 3/2008 | Lu | |
| 7,459,673 B2 | 12/2008 | Katori | |
| 7,915,060 B2 | 3/2011 | Toyama | |
| 7,963,775 B2 * | 6/2011 | Reisinger | H01R 12/7082 |
| | | | 439/67 |
| 8,485,511 B2 * | 7/2013 | Di Stefano | G01R 31/2867 |
| | | | 269/303 |
| 8,683,674 B2 * | 4/2014 | Di Stefano | G01R 31/2867 |
| | | | 29/596 |
| 8,739,392 B2 | 6/2014 | Byquist | |
| 2002/0125124 A1 | 9/2002 | Lake | |
| 2003/0096514 A1 | 5/2003 | Ho | |
| 2004/0067674 A1 | 4/2004 | Hirata | |
| 2004/0144927 A1 | 7/2004 | Auner | |
| 2005/0124189 A1 | 6/2005 | Mohnescu | |
| 2005/0245106 A1 | 11/2005 | Ma | |
| 2006/0024990 A1 * | 2/2006 | Ahmad | G01R 1/0483 |
| | | | 439/71 |
| 2007/0007956 A1 | 1/2007 | Min | |
| 2008/0303135 A1 | 12/2008 | Pang | |
| 2012/0073864 A1 | 3/2012 | Stefanoff et al. | |
| 2013/0285242 A1 | 10/2013 | Watts | |

* cited by examiner

IN-PLACE CLAMPING OF PIN-GRID ARRAY

BACKGROUND

"Atomtronics", a contraction of "atom" and "electronics", refers to devices that are analogous to integrated circuits, but that are designed to sense and manipulate atom-scale particles, including neutral atoms, monatomic ions (ionized atoms), and polyatomic ions (ionized molecules). Applications include the study of ultra-cold states of matter, atomic clocks, and quantum computing.

It can be difficult to sense and manipulate individual particles when they are continually colliding with neighboring particles. To reduce the frequency of collisions so that particles have a useful mean-time between collisions (i.e., a sufficient mean free path), the particles sensed and manipulated by atomtronics are typically in a vacuum; herein "vacuum" encompasses volumes at pressure at most an order of magnitude below 1 atmosphere (atm). More specifically, "vacuum" encompasses "high vacuum (HV), ultra-high vacuum (UHV), extreme-high vacuum (XHV), and variants of these.

Atomtronic devices may be contained within a vacuum to provide a desired proximity to the particles to be sensed and manipulated. However, locating the devices within the vacuum can be problematic in that the connections through the vacuum boundary required to interface with external instrumentation can be sites for vacuum compromise.

U.S. Pat. No. 7,126,112 describes an atomtronic device, in this case, an atom chip, that completes a vacuum boundary of a vacuum chamber and includes photolithographically defined vias for transferring electrical signals to and from the vacuum interior from and to equipment exterior to the vacuum. Active elements of the atomtronic device are exposed to the vacuum, while the vias provide robust links between the vacuum and the ambient. Like some computer chips, such atomtronic devices can be packaged in a pin-grid array (PGA). The PGA can be inserted into a socket, which can provide a physical and electrical interface with a printed-circuit board or other system for controlling and sensing quantum effects within the UHV chamber.

DETAILED DESCRIPTION

The present invention provides a compact socket with a dual-cam camshaft to move a pair of socket plates in opposite directions relative to a socket frame to clamp-in-place pins of a pin-grid array (PGA). In one relative position of the plates, holes in the upper plate are aligned with holes in the lower plate so that pins of a PGA can be inserted into the socket with zero or low insertion force. Moving the plates in opposite directions causes the socket plate holes in the respective plates to be misaligned symmetrically; in the process, socket contacts in the holes of the respective plates to be forced against opposite sides of the pins, whereby the pins are likewise symmetrically clamped in place, i.e., the pins do not move relative to the socket frame in the course of the clamping.

In a prior-art design, a single-cam camshaft moves a single plate to drive a contact prong against a PGA pin and then to drive the prong and pin against a second prong to ensure a good electrical connection. In the process, the pin is deflected, inducing stress in the pin. If the device package including the PGA is free to move, the stress can be relieved by allowing the package to move in the direction of the deflection. Also, the single-cam camshaft is located outside the footprint of the PGA, so the socket is less compact than the socket disclosed herein.

However, in the context of a system of interest herein, the device package, in this case, an atomtronic package, is not free to move. Instead, a frame of the PGA socket is rigidly coupled to a vacuum cell structure to which the atomtronic package is sealed. Instead of moving the atomtronic package, the pin deflection would apply a stress to the seal, risking a compromise to a vacuum within the vacuum cell. The present invention, by clamping the pins in place (without deflecting the pins) protects the pins from external stresses and impacts and, thus, avoids this risk to vacuum integrity.

Figure 1:
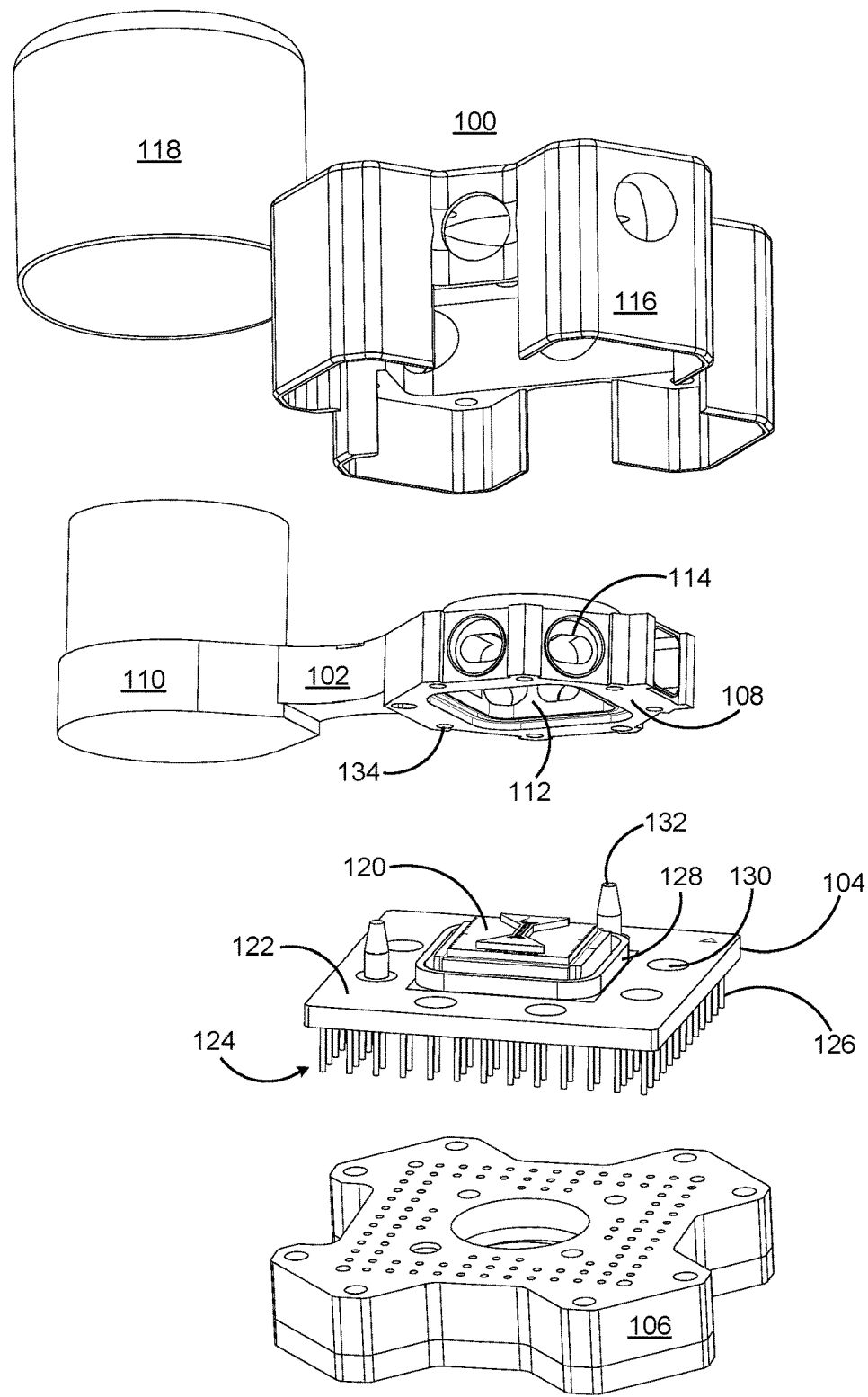
FIG. 1 is a mixed isometric perspective exploded diagram of an atomtronic system.

An atomtronic system 100 is shown in FIG. 1 including a vacuum-cell structure 102, an atomtronic package 104, and a clamp-in-place socket 106. Vacuum-cell structure 102 includes a vacuum chamber 108 and a sputter ion pump 110. Vacuum chamber 108 has an aperture 112 to be closed and sealed by the atomtronic package 104. Vacuum chamber 108 includes windows 114 that provide optical access to the chamber interior. A shield 116 protectively covers vacuum chamber 108, the atomtronic package 104, and socket 106. A cover 118 protects and magnetically shields ion pump 110.

Atomtronic package 104 includes an atomtronic device 120 (e.g., an atom chip or an ion chip), a base 122, and a pin-grid array 124 of pins 126. Atomtronic device 120 is designed to manipulate atom-scale particles within a vacuum chamber. Atomtronic device 120, when sealed to vacuum chamber 108 has active elements exposed to the vacuum interior for manipulating and sensing quantum and other particles. Atomtronic package 104 also includes a soft-metal (indium) gasket 128 surrounding atom chip 120 for providing a hermetic seal between atomtronic package 104 and vacuum chamber 108. Eight holes 130 distributed around the periphery of socket base 122 receive alignment pins 132 (two shown) for aligning atomtronic package 104 with vacuum chamber 108 upon assembly. Alignment pins 132 are tapered to guide them into alignment holes 134 of vacuum-cell structure 102.

Figure 2:
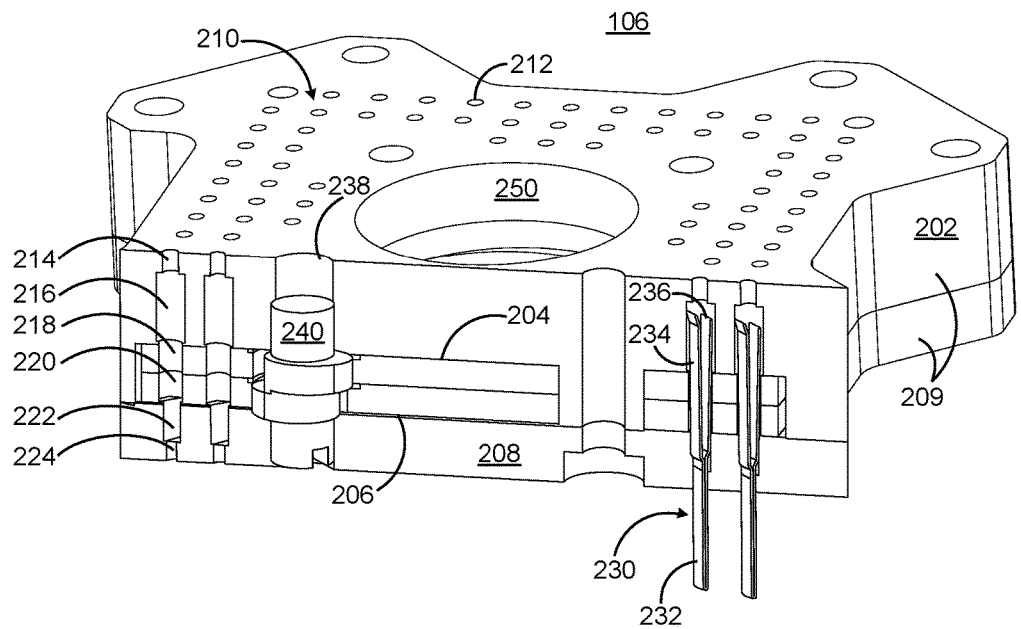
FIG. 2 is a cut-away perspective view of a socket of the atomtronic system of FIG. 1.

As shown in FIG. 2, clamp-in-place socket 106 includes a cover 202, an upper plate 204, a lower plate 206, and a base 208. In the illustrated embodiment, plates 204 and 206 are identical so as to save manufacturing costs; in alternative embodiments, the plates are not identical. Socket 106 includes an array 210 of socket holes 212 for receiving pins 126 of PGA 124 (FIG. 1). Cover 202 and base 208 are bolted together to constitute a socket frame 209. Each socket hole 212 includes a narrow cover hole 214, a wide cover hole 216, an upper plate hole 218, a lower plate hole 220, a base groove 222, and a base hole 224.

Each of the socket holes 212 is occupied by a socket contact 230 (two shown in FIG. 2). Each socket contact includes a stem 232, an upper prong 234, and a lower prong 236. ("Upper" and "lower" as applied to the prongs indicates which plate (upper or lower) is to move the prong into the clamping position.) For each contact 230, its stem extends through and below the respective narrow base hole 224, its stem and prongs meet in base groove 222, and its prongs extend from base groove 222, through the respective lower plate hole 220, through the respective upper plate hole and into the respective wide cover hole 216.

Cover 202, plates 204 and 206, and base 208 are of non-conductive material. In various embodiments, the non-conductive material can be a plastic such as polyether ether keytone (PEEK), a polyoxymethylene (such as DuPont™ Delrin®, or a ceramic such as alumina. Glass or low conductivity silicon may also be used to achieve CTE (Coefficient of Thermal Expansion) matching. To ensure sufficient resistivity, float-zone or undoped silicon can be used. Alternatively, an insulating oxide or nitride or other insulator film of sufficient thickness can cause the silicon to achieve sufficient resistivity.

Figure 3:
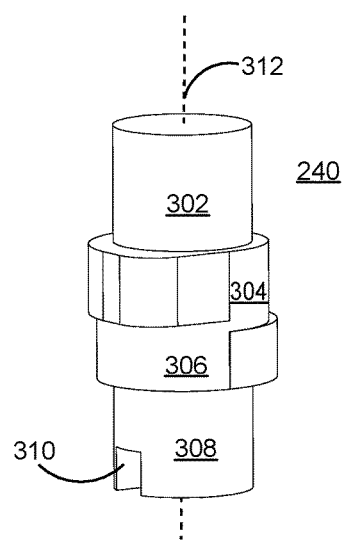
FIG. 3 is a perspective view of a camshaft of the socket of FIG. 2.

Socket 106 also has a camshaft hole 238 for holding a camshaft 240. As shown in FIG. 3, camshaft 240 includes a top cylindrical section 302, an eccentric upper cam 304, an eccentric lower cam 306, and a bottom cylindrical section 308. Bottom cylindrical section 308 includes a slot 310 that can be engaged by a flat-head screwdriver for the purpose of changing orientation of camshaft 240 about a rotational axis 312 that is the axis of cylindrical symmetry for cylindrical sections 302 and 308. Comparing FIGS. 2 and 3, it can be seen that top cylindrical section 302 extends into cover 202, upper cam 304 is vertically aligned with upper plate 204, lower cam is vertically aligned with lower plate 206, and bottom cylindrical section 308 extends through base 208.

Figure 4:
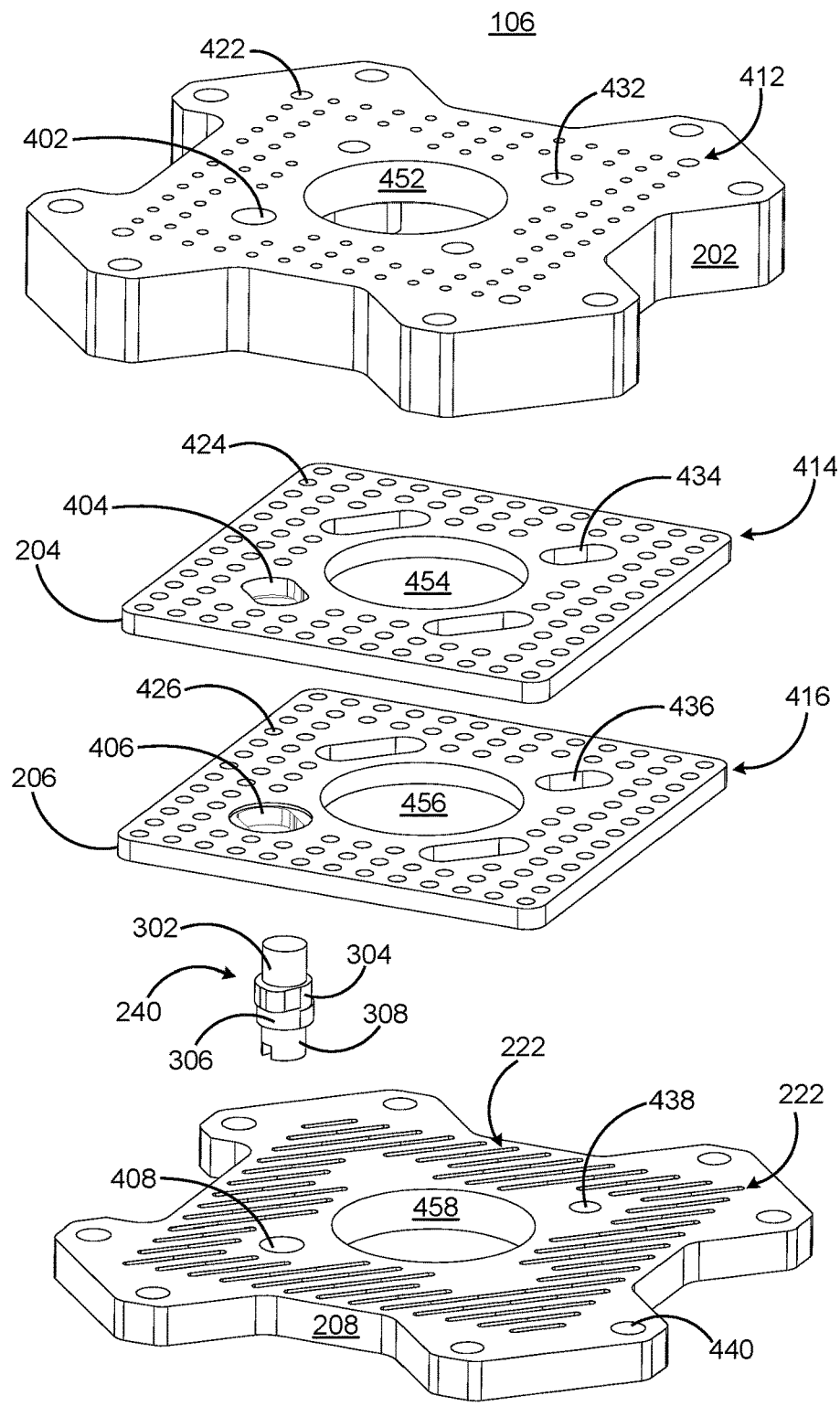
FIG. 4 is a top isometric exploded view of the socket of FIG. 2.
Figure 5:
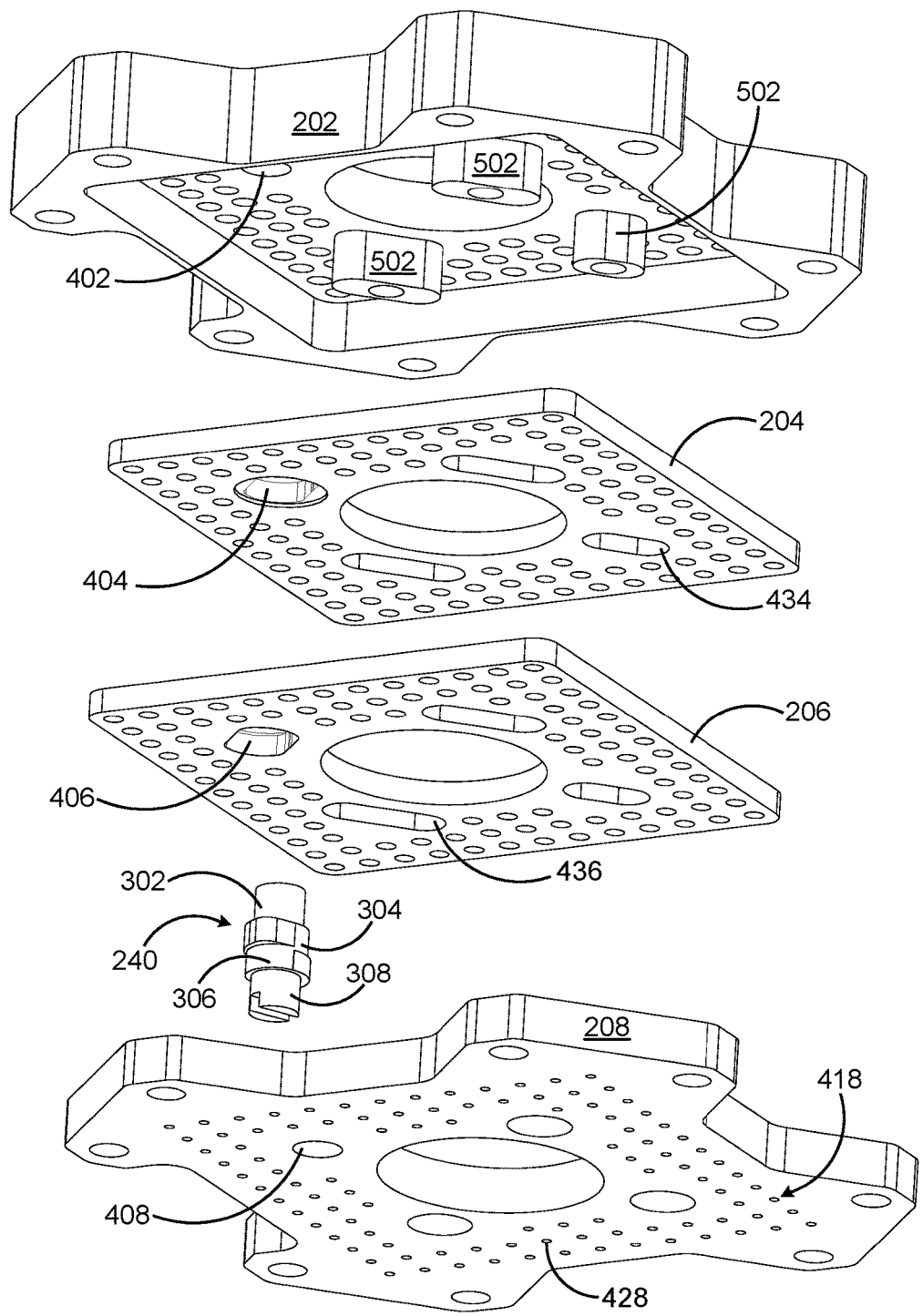
FIG. 5 is a bottom isometric exploded view of the socket of FIG. 2.

As indicated in FIGS. 4 and 5, top cylindrical section 302 of camshaft 240 turns within a circular hole 402 of cover 202, upper cam 304 turns within an oblong hole 404 of upper plate 204, lower cam 306 turns within an oblong hole 406 of lower plate 206, and bottom cylindrical section 308 turns within a cylindrical hole 408 through base 208. Each of cover 202, upper plate 204, lower plate 206, and base 208 includes a respective array 412, 414, 416, and 418 of holes 422, 424, 426, and 428, encompassing sections 214-224 (FIG. 2) of holes 212 of array 210 of socket 106. Array 418 and holes 428 are best seen in FIG. 5; holes 428 extend downward from the base of grooves 222, shown in FIG. 4.

The drive mechanism, i.e., camshaft 240, for socket 106 is located entirely within the "footprint" of pin-grid array 124. Thus, in FIGS. 4 and 5, it can be seen that the camshaft holes 402, 404, 406, and 408 (through and into which camshaft 240 extends) are all surrounded respectively by contact holes 422, 424, 426, and 428 (FIG. 5). For example, in FIG. 4, it can be seen that there are contact holes 424 between camshaft hole 404 and each of the four sides of upper plate 414. Having the drive mechanism entirely within the PGA footprint allows for a socket that is more compact than alternative designs in which the drive mechanism is located partially or entirely off to the side of the PGA. The greater compactness of the socket allows the incorporating atomtronic system 100 to be more compact and thus more portable and less expensive.

A relatively large center hole 250 (FIG. 2) provides for optical access to the back or ambient side of the atomtronic device 120 (FIG. 1). Center hole 250 provides for high numerical aperture (NA) optical interrogation or manipulation of the respective atoms or ions; atomtronic devices typically have a window made of glass or similar material transparent to the wavelength of interest. Typically, the wavelength of interest is within the visible or near infra-red (NIR) range. Center hole 250 extends through cover 202, plates 204 and 206, and base 208. Accordingly there are respective center holes 452, 454, 456, and 458 as shown in FIG. 4.

There are also three stacks of spacer holes through socket 106, including circular spacer holes 432 in cover 202, elongated spacer holes 434 in upper plate 204, elongated spacer holes 436 in lower plate 206, and circular spacer holes 438 in base 208. Comparing FIGS. 4 and 5, one can see that spacer holes 432 (FIG. 4) in cover 202 are used to attach elongated spacers 502 (FIG. 5), which extend through elongated spacer holes 434 in upper plate 204 and elongated spacer holes 436 in lower plate 206. Bolts (not shown) extending through the spacers 502 can be used to fix the cover and base to each other to constitute socket frame 209 (FIG. 2). Spacers 502 maintain a spacing between cover 202 and base 208 so that plates 204 and 206 have room to move relative to the base 208 and cover 202.

Spacer holes 434 and 436 are more elongated than the spacers 502 they receive to permit the plates 204 and 206 to move in the direction of elongation relative to base 208 and cover 202, and each other. The transverse dimensions of spacers 502 and elongated holes 434 and 436 are more closely matched so as to confine movement of plates 204 and 206 to along the direction of elongation.

Figure 6:
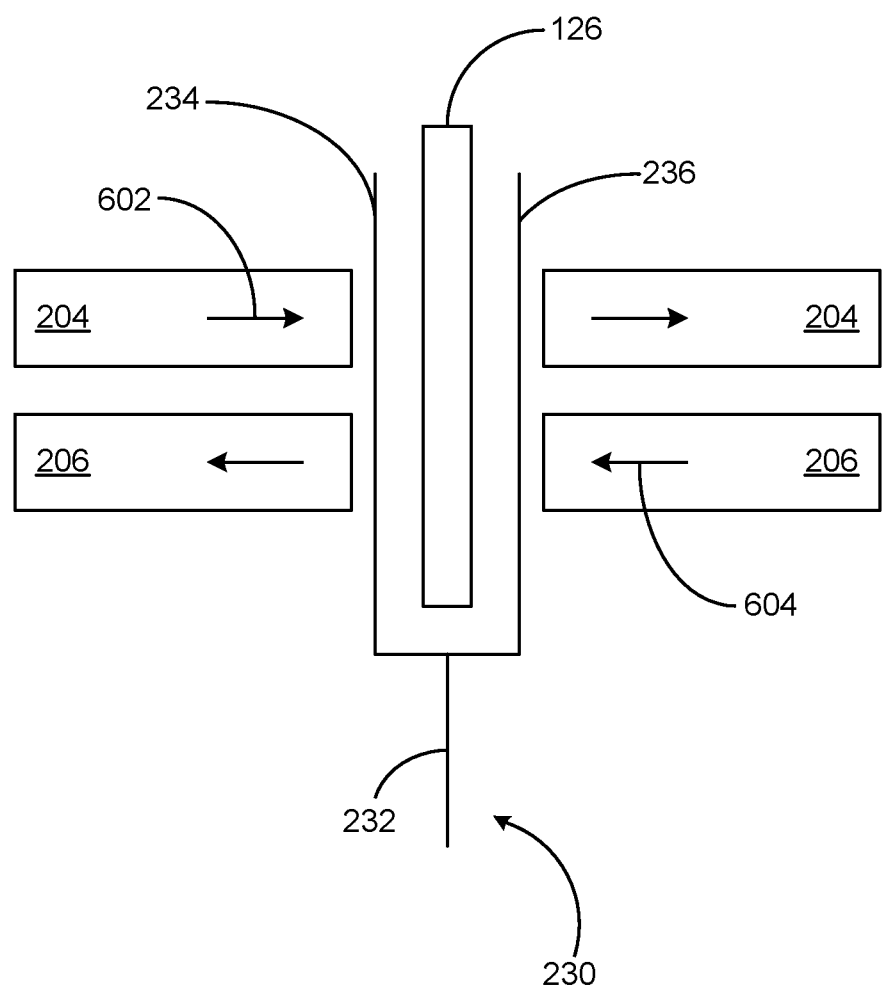
FIG. 6 is a schematic illustration of how plates (of the socket of FIG. 2) driven by the camshaft of FIG. 3 can be used to clamp a pin between prongs of a contact of the socket of FIG. 2.

As indicated in highly schematic FIG. 6, parallel plates 204 and 206 are to move in opposite directions (anti-parallel) to each other. Thus, as upper plate 204 is moved to the right, as indicated by arrow 602, lower plate 204 moves by a like amount to the left as indicated by arrow 604. The movement indicated in FIG. 6 is designed to bend contact prongs 234 and 236 toward each other and press them against PGA pin 126 to clamp it in place and ensure good electrical connection. Of course, plates 204 and 206 can be moved antiparallel in directions opposite those indicated in FIG. 6 to release pin 126.

Figure 7:
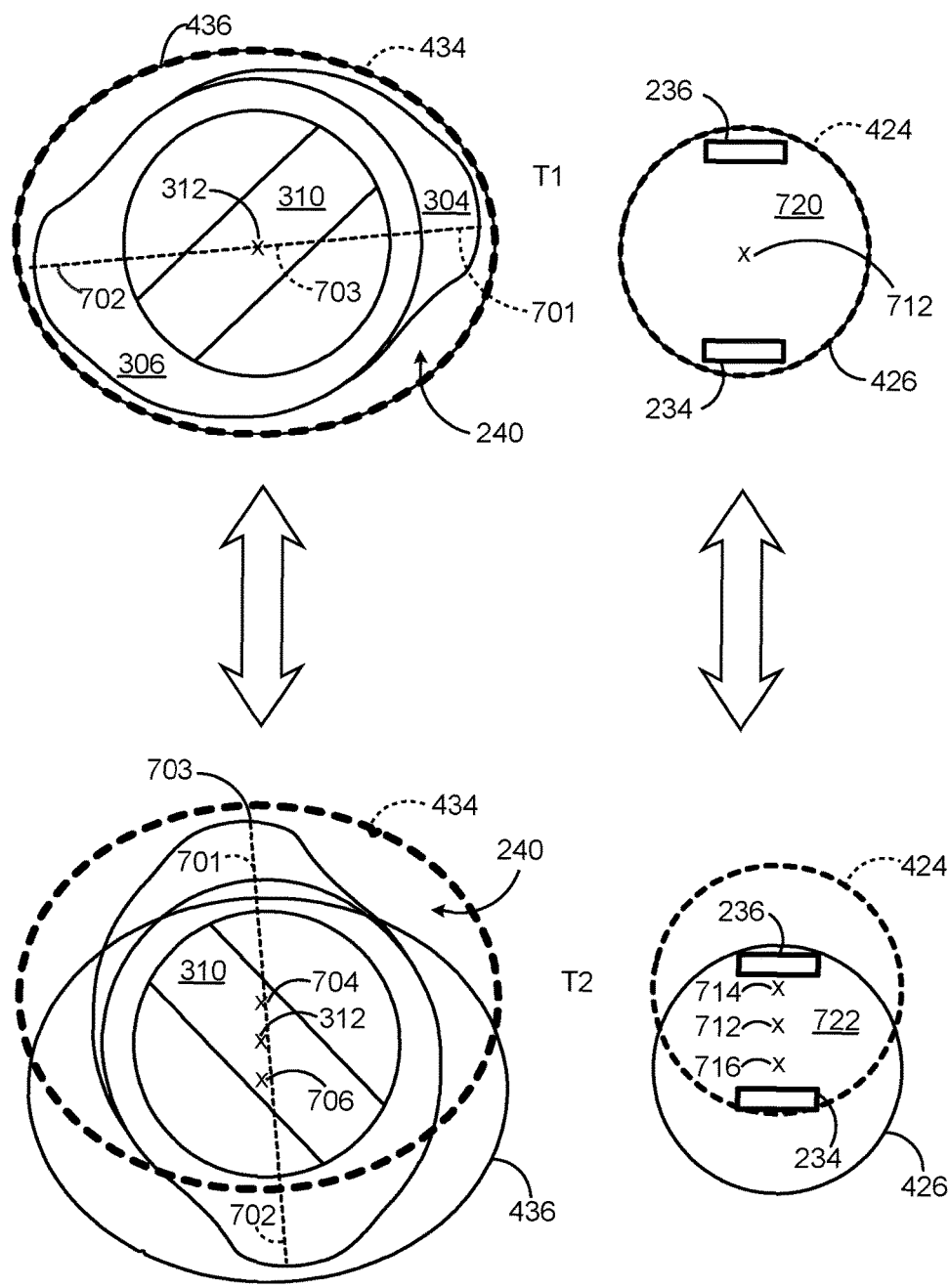
FIG. 7 is a schematic illustration of the effect the movement of the plates has on the alignment of holes in the plates and on the contact prongs that extend through those holes.

The role of camshaft 240 in controlling the antiparallel motion of plates 204 and 206 is indicated in the bottom view of FIG. 7. At time T1, camshaft 240 is in its "release" orientation. Upper cam 304 has a major (longest) radius 701 that extends in a first direction from axis 312 to the periphery of upper cam 304. Lower cam 306 has a major radius 702 that extends in a second direction from axis 312 to the periphery of lower cam 306. The direction in which the major radius 702 extends is opposite the direction in which major radius 701 extends. Collectively, major radii 701 and 702 constitute a major (longest) diameter 703 for camshaft 240.

Major diameter 703 is generally aligned with the major diameters of cam holes 404 and 406 in upper and lower plates 204 and 206. Lower plate hole 436 is represented, in FIG. 7, by a relatively thin solid line, while upper plate hole 434 is represented, in FIG. 7, by a relatively thick dashed line. These holes 434 and 436 are aligned in the time T1 release orientation, and their centers are aligned with the axis 312 of rotation for camshaft 240. Likewise, pin holes 424 and 426 are aligned at time T1 so that prongs 234 and 236 of a contact 230 can be separate. With the prongs so separated, a pin can be inserted between prongs 234 and 236. Alternatively, if a pin has been inserted, it can be readily removed when prongs 234 and 236 are separated as at T1.

The orientation of camshaft 240 can be changed, e.g., using a flat-head screwdriver inserted into slot 310, to the "clamp" orientation show for time T2. Cam holes 434 and 436 can be co-designed with cams 304 and 306 to provide detents (not shown), i.e., potential minima at the clamp orientation of the camshaft. These detents provide feedback to a user when the clamp orientation is reached and provide resistance to accidental deviations from the clamp orientation. In a variation, detents are also provided for a maximal open orientation.

As shown in the lower portion of FIG. 7, major diameter 703 of camshaft 204 is aligned at time T2 with the minor diameters of cam holes 434 and 436 (instead of with the major diameters of cam holes 434 and 436 at time T1). Plates 204 and 206 (FIG. 6) have moved antiparallel to each other such that cam holes 434 and 436 are now offset; note that the center 704 of upper plate hole 434 is displaced from the center 706 of lower plate hole 436, and both holes 434 and 436 are displaced from the axis 312 of rotation for camshaft 240.

Correspondingly, contact holes 424 and 426 have been moved antiparallel so that their respective centers 714 and 716 have been displaced from their previous common position 712 to positions on either side. As a result, an area 720 of an intersection of projections onto a plane (e.g., represented by the sheet on which FIG. 7 is formed) of holes of the first array and holes of the second array in the open position is larger than the area 722 of the intersection in the clamped orientation.

Lower plate 206 has urged lower prong 236 toward upper prong 234, while upper plate 204 has urged upper prong 234 toward lower prong 236. Thus, prongs 234 and 236 are closer together in the "clamp" orientation of time T2 than they are in the "open" orientation of time T1. A pin that had been inserted between prongs before they were urged together would be clamped between them given their positions at time T2. Of course, the pin could then be released by returning camshaft 240 to its "open" orientation.

Figure 8:
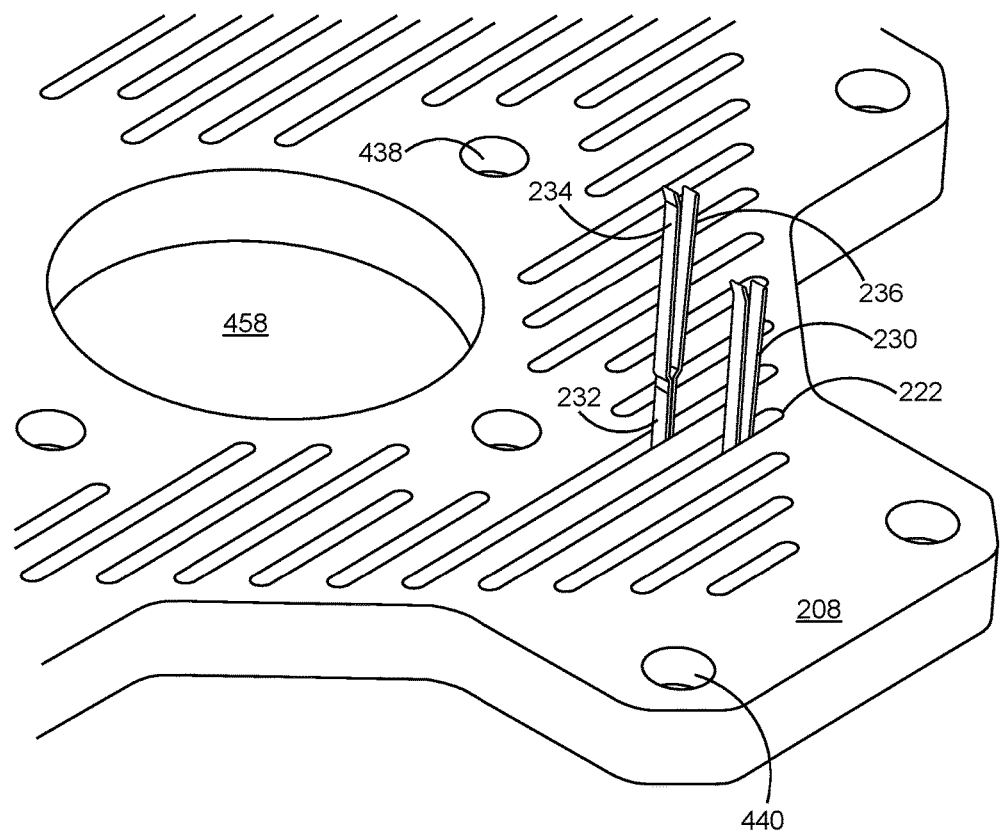
FIG. 8 is a perspective view of a portion of the base of the socket of FIG. 2 showing how contacts can be seated in grooves of the base so that their rotational positions are fixed.

As shown in FIG. 8, grooves 222 are formed in base 208. These grooves extend parallel to the directions of antiparallel motion of plates 204 and 206 (FIG. 6). The prongs 234 and 236 of each contact 230 are seated at the base of the respective groove. The widths of the grooves and the prongs are matched so that the prongs cannot rotate relative to the grooves. This ensures that the prongs of a contact oppose each other along the directions of antiparallel motion of the plates so that moving the plates can be used to urge the prongs together, e.g., to clamp PGA pins. The stems 232 of the contacts 230 extend through circular holes 222 (FIGS. 2 and 5) that extend from the bottoms of grooves 222 to the bottom of base 208. Note that in FIG. 8, contacts are shown both in the process of being inserted and fully seated in the respective groove.

Figure 9A:
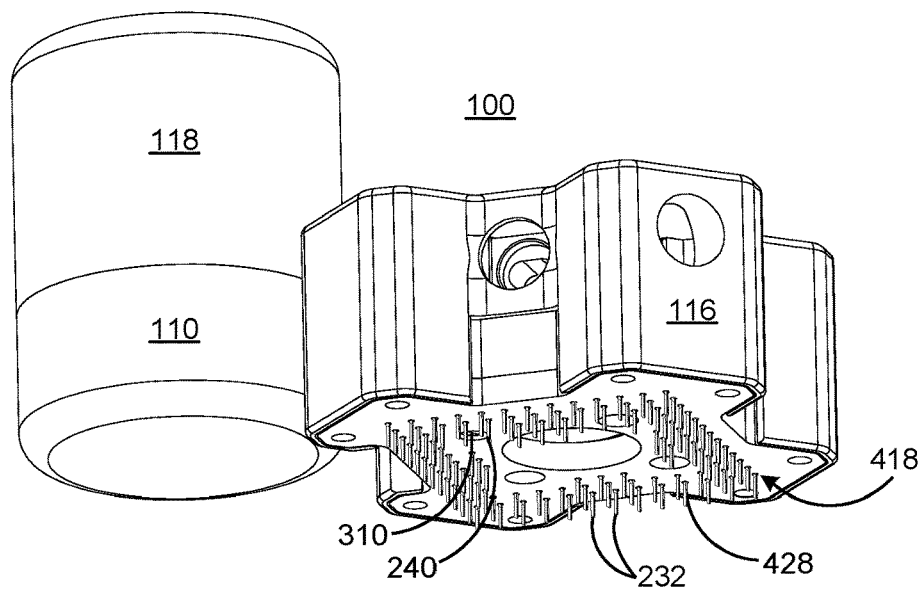
FIGS. 9A and 9B are, respectively, bottom and top perspective views of the atomtronic of FIG. 1 after it is assembled.
Figure 9B:
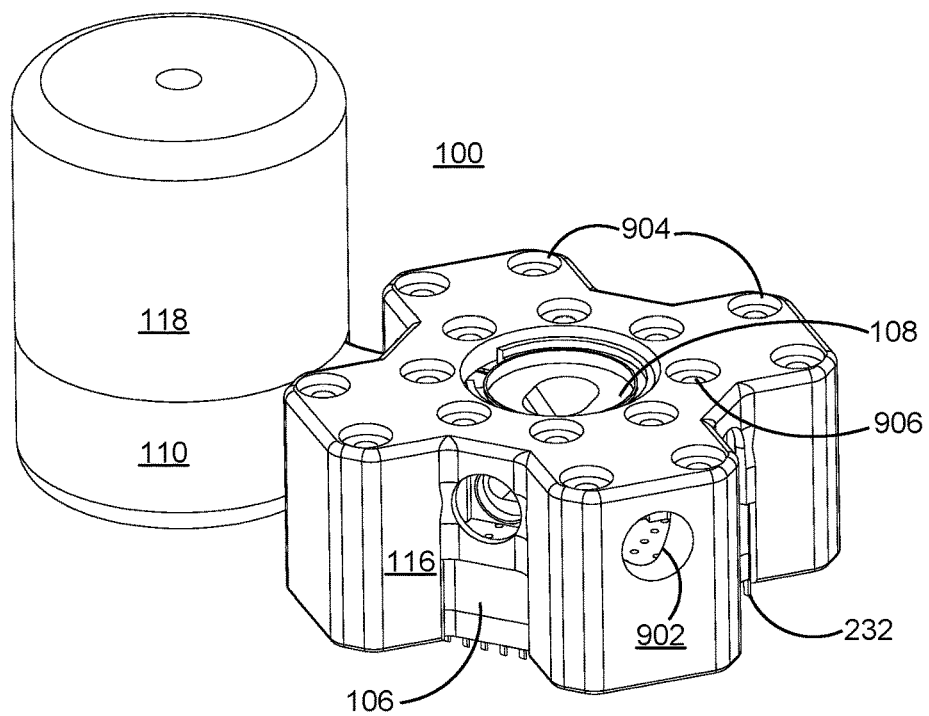

FIGS. 9A and 9B represent the assembled atomtronics system 100. As shown in FIG. 9A, stems 232 protrude down through the bottom of base 208 so they are accessible for interfacing with PC boards, plugs, and other external devices. Also, as shown in FIG. 9A, slot 310 of camshaft 240 is accessible from the bottom of socket 106.

As shown in FIG. 9B, shield 116 includes ports 902 that align with windows 114 (FIG. 1) in the vacuum cell 108 to provide optical access to the interior of the vacuum cell 108. Shield 116 has eight peripheral holes 904 that accommodate bolts that are screwed into respective holes 440 (FIG. 4) in the socket base 208. Shield holes 906 accommodate bolts for attaching shield 116 to vacuum cell 108. Thus, shield 116 rigidly couples socket base 208 to vacuum cell 108 so that the socket 208 and vacuum cell 108 cannot move relative to each other to relieve stress, e.g., induced by flexing of PGA pins. The present invention, thus, avoids stress that might otherwise compromise the indium gasket by avoiding deflection of the PGA pins when establishing electrical connections with the socket contacts.

Figure 10:
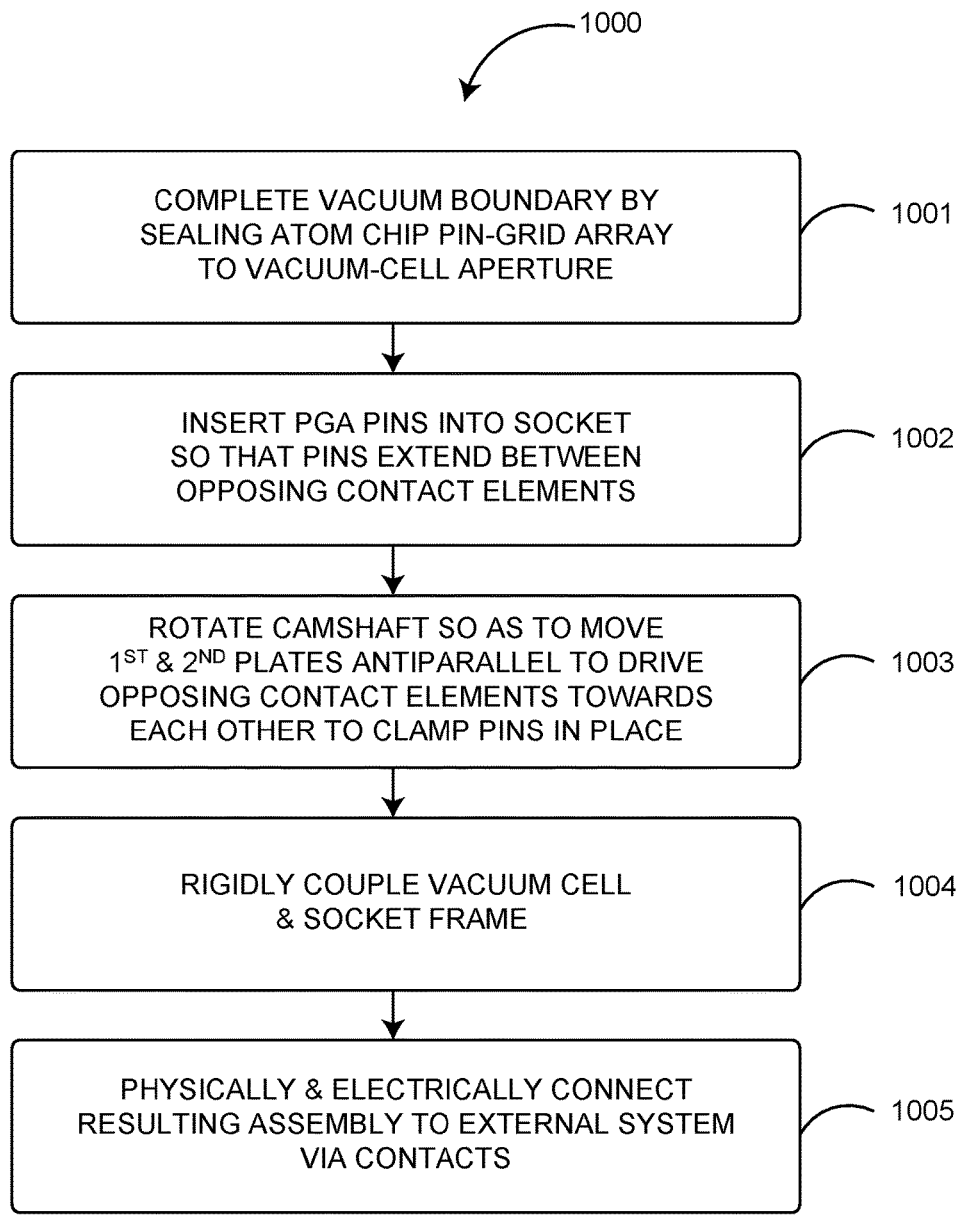
FIG. 10 is a flow chart of a process for assembling the atomtronic system of FIG. 1.

An atomtronics process 1000 is flow charted in FIG. 10. At 1001, a vacuum boundary of a vacuum cell is completed by sealing an aperture in a vacuum-cell structure with an atomtronics package including a pin-grid array, e.g., an atom-chip (ACPGA) or ion-chip pin-grid array (ICPGA). At 1002, pins of the ACPGA are inserted between opposing elements, e.g., prongs, of a socket contact. More specifically, pins are inserted through contact holes of a cover of a frame, holes of a first plate, and holes of a second plate.

At 1003, socket plates are moved antiparallel to each other and in opposite directions with respect to the frame. This movement drives the contact elements against respective pins so as to clamp the pins in place (without deflecting or otherwise changing the pin positions or orientations). More specifically, the pins are not moved relative to the socket frame. Note that the plates can be moved antiparallel to each other by driving them using a camshaft with two cams arranged with a 180° orientation with respect to each other.

At 1004, the vacuum cell and the socket frame can be rigidly coupled to each other, e.g., by attaching a shield to both the frame and the vacuum cell. This coupling occurs at an established plane of contact parallel to the pin array and fastener. Features provide sufficient "slop" or tolerance to allow clamping over a minor deviation in plane to allow for stack-up tolerances in the assemblies; this results in zero sheer force on the pin-grid array and, therefore, the atom/ion chip. At 1005, the resulting assembly can be physically and electrically connected to external devices via the socket contacts. These steps can be reversed to release the PGA pins so that the atomtronics package can be disengaged from the socket.

While it is described above in the context of an atomtronics system, the present invention has wide applicability to situations in which bending or applying stress to pins is undesirable. Applications include ultra-cold-matter physics, ion traps, superconducting chips, quantum dot chips, or anything requiring a vacuum and a large array of feedthroughs for a compact integrated-circuit-like structure.

In the illustrated embodiments, the antiparallel motion of identical plates is controlled using a dual-cam camshaft that is within the area of the pin-grid array. However, there is not always room in the interior of a PGA for such a camshaft. So an alternative is to locate the dual-cam camshaft outside the array.

In another embodiment, a dual-cam camshaft lies with its rotational axis horizontal (instead of vertical); in this embodiment, the plates are not identical so that the cams engage each plate in a different direction. In another embodiment, the drive mechanism is a screw with counter handed threads that each opposing handedness engages each plate directly or through an intermediate motion actuator.

In another embodiment, a wedge is driven orthogonal to the axis of motion by a screw or spring rod whereby the wedge pushes on asymmetric features of each plate to drive the plates in opposite directions. In another embodiment a ratchet device leverages rotation or linear motion of a screw, rod, or wedge with teeth or plateaus to ratchet and, stably or quasi-stably, locks the plates to varying depths of displacement.

A Wikipedia article entitled "Atomtronics" states that "Atomtronics is an emerging sub-field of ultra-cold atomic physics which encompasses a broad range of topics featuring guided atomic matter waves. The systems typically include components analogous to those found in electronic or optical systems, such as beam splitters and transistors." "Atomtronics", as used herein, encompasses the meaning given by the article, but also covers other uses, e.g., ion traps, in which a device is used to manipulate atom-scale particles (including monoatomic ions and polyatomic ions) in a vacuum. An "atomtronic device" is a photolithographically defined, or direct micro/nano-printed/assembled structure that can include electrical, optical, and mechanical elements. The atomtronic structures may be linear, planar, or three-dimensional. An "atomtronic package" is an assembly of an atomtronic device, a conductor-grid array (such as a pin-grid array, via-grid array, or pad-grid array), and elements for protecting the device and interfacing the device with the conductor-grid array.

Herein, a "frame" is a rigid structure that surrounds or encloses something; in the present case, the frame (cover plus base) surrounds the plates. A plate is a thin, flat, rigid sheet of material. An "array" is an ordered series or arrangement. A "drive mechanism" is an object or device that receives power and applies it to moving another object.

In coordinate geometry, a "ray" is a straight one-dimensional entity that starts at a point with given coordinates, and goes off in a particular direction to infinity, possibly through a second point. Herein, "translational direction" is what parallel rays share, but non-parallel rays do not. In coordinate geometry, a straight line extends in two opposing translational directions. Herein, "rotational direction" encompasses "clockwise" and "counterclockwise". Unless otherwise clear from context, herein, "direction" refers to a "translational direction."

Herein, a "radius" is a ray segment extending from a centroid of a shape to a point on the perimeter of the shape. Radii of a circle are all the same length but the radii for other geometric objects, e.g., a cam cross section, can have different lengths; in such cases, a radius with the greatest length among radii of the object is referred to as a "major radius".

Herein, "state" is the particular condition that something is in at a specific time. Herein, a "guide mechanism" is a device or other object that constrains another object's direction of movement. Herein, a "projection" is a transformation of points and lines in one or source planes onto a target plane by connecting corresponding points on source planes with points on the target plane using parallel line segments.

Herein a "prong" is each of two or more projecting elements at the end of a fork or similarly shaped object. Herein, "rotationally coupled" means attached in a way that permits one of the attached objects to rotate. Herein, "hermetic" is the quality of something—a seal, a container, structure, etc.—being airtight (excluding passage of air, oxygen, or other gases). Used technically, it is stated in conjunction with a specific test method and conditions of use."

Herein, a pin-grid array is deemed as occupying a volume that is the smallest convex volume including the full extension of all pins of the array. This volume is as deep as the pins are long and has a cross section corresponding to a perimeter that surrounds the pins. Herein, a volume is "convex" if and only if any line between two points in the volume is entirely included within the volume. In one of its aspects, the present invention provides for locating the camshaft so that it extends into the pin-grid array; since the rotational axis can be parallel to the pins of the pin-grid array, the entire cam shaft can be located either within or below (as defined by the directions in which the pins extend into the socket) the pin-grid array. This is as opposed to occupying volume laterally outside the pin-grid array. As result, the socket of the invention is compact relative to sockets with drive mechanisms that extend off to the side of a pin-grid array.

Herein, art labeled "prior art", if any, is admitted prior art. Art not labeled "prior art", if any, is not admitted prior art. The illustrated embodiments, variations thereupon, and modifications thereto are provided for by the present invention, the scope of which is defined by the following claims.

What is claimed is:
1. A system comprising:
  a frame;
  a first plate coupled to the frame so as to permit motion of the first plate relative to the frame, the first plate including a first array of contact holes, the first plate having a first camshaft hole, the first camshaft hole having a non-circular cross section;
  a second plate coupled to the frame so as to permit motion of the second plate relative to the frame, the second plate including a second array of contact holes, the second plate having a second camshaft hole, the second camshaft hole having a non-circular cross section;
  contacts mechanically coupled to the frame and extending through respective contact holes of the first array and through respective contact holes of the second array, each of the contacts being electrically conductive; and
  a camshaft coupled to the frame so as to permit rotational movement of the camshaft relative to the frame, the camshaft extending through the first camshaft hole of the first plate and through the second camshaft hole of the second plate, the camshaft having a first cam and a second cam, the first cam and the second cam being respectively coupled to the first plate and the second plate so that, when the camshaft is rotated, the first plate and the second plate move in opposite directions relative to the frame.

2. The system of claim 1 wherein each of the contacts includes a first element and a second element, the camshaft having a clamp orientation and a release orientation such that rotating the camshaft from its release orientation toward its clamp orientation causes the first element and the second element to move in opposite directions so as to approach each other.

3. The system of claim 2 wherein, while pins of a pin-grid array remain inserted into the contact holes of the first array:
  rotating the camshaft from the release orientation to the clamp orientation causes the first and the second elements of each contact to clamp-in-place a respective pin; and rotating the camshaft from the clamp orientation to the release orientation causes the first and second elements of each contact to release the respective pin.

4. The system of claim 2 wherein the first plate has four sides, for each of the sides, there being at least one contact hole between that side and the first camshaft hole.

5. The system of claim 2 wherein the first cam has a first major radius that extends from an axis of rotation for the camshaft in a first radius direction opposite to a second radius direction in which a second major radius of the second cam extends from the axis of rotation.

6. The system of claim 2 wherein the frame includes a cover and a base, the first plate being disposed between the cover and the second plate, the second plate being disposed between the first plate and the base, the cover including a third array of holes such that pins of the pin grid array are inserted through the holes of the third array before they are inserted into the holes of the first array, the camshaft being rotationally coupled to the base and to the cover.

7. The system of claim 6 wherein the frame includes a guide mechanism rigidly coupled to the cover and to the base and extending through the first plate and the second plate so as to confine movement of the first and second plates to the opposite directions.

8. The system of claim 6 further including an atomtronic package including a pin-grid array (PGA) of electrically conductive pins, the pins being inserted into respective contact holes of the first, second, and third arrays of holes.

9. The system of claim 8 wherein the PGA has a footprint, the camshaft being disposed entirely in the footprint.

10. The system of claim 8 further comprising a vacuum-chamber, the atomtronic package being hermetically sealed with the vacuum chamber to define a vacuum boundary between a vacuum interior and a vacuum exterior, the atomtronic package including an atomtronic device with a surface exposed to the vacuum interior, the pins of the PGA being in the vacuum exterior, the vacuum chamber being rigidly coupled to the frame.

* * * * *